United States Patent [19]

Baskeyfield et al.

[11] Patent Number: 5,475,023
[45] Date of Patent: Dec. 12, 1995

[54] AQUEOUS PHARMACEUTICAL FORMULATIONS OF SODIUM CROMOGLYCATE

[75] Inventors: Lewis J. Baskeyfield, Holmes Chapel; Graham F. Jay, Cheshire; Steven P. Probert, Northwich, all of England

[73] Assignee: Fisons plc, Ipswich, England

[21] Appl. No.: 281,792

[22] Filed: Jul. 28, 1994

Related U.S. Application Data

[63] Continuation of Ser. No. 27,356, Mar. 8, 1993, abandoned.

[30] Foreign Application Priority Data

Jul. 7, 1992 [GB] United Kingdom .................. 9214390

[51] Int. Cl.$^6$ ...................... A61K 31/35; A61K 31/045; A61K 47/00
[52] U.S. Cl. ........................... 514/456; 514/738; 514/772
[58] Field of Search ..................................... 514/456, 738, 514/772

[56] References Cited

U.S. PATENT DOCUMENTS

| | | | |
|---|---|---|---|
| 3,975,536 | 8/1976 | Stevenson et al. | 424/283 |
| 4,053,628 | 10/1977 | Stevenson et al. | 424/283 |

FOREIGN PATENT DOCUMENTS

| | | |
|---|---|---|
| 0413583A2 | 2/1991 | European Pat. Off. . |
| 1473318 | 5/1974 | United Kingdom . |
| 1593097 | 7/1981 | United Kingdom . |
| PCT/GB90/00637 | 11/1990 | WIPO . |

OTHER PUBLICATIONS

Research Disclosures 318, pp. 832–833 (No. 31850) Oct. 1990 (Anonymous).

*Drug Design and Delivery*, 1987, vol. 1, pp. 285–295, "Enhanced Percutaneous Absorption of Ionizable Water–soluble Drugs."

*Journal of Pharmaceutical Sciences*, Jan. 1988, vol. 77, No. 1, pp. 3–14, "Mechanisms of Corneal Drug Penetration I: In Vivo and In Vitro Kinetics."

*Primary Examiner*—Raymond Henley, III
*Assistant Examiner*—M. Moezie
*Attorney, Agent, or Firm*—Marshall, O'Toole, Gerstein, Murray & Borun

[57] ABSTRACT

A pharmaceutical formulation comprising a substantially clear aqueous solution having a viscosity of less than 10 mPa.s containing 3.5 to 5% w/v of 1,3-bis(2-carboxychromon-5-yloxy)-propan-2-ol, or a pharmaceutically acceptable salt thereof, as active ingredient and glycerol, the concentration of ions of metals of groups IIA, IB, IIB and IVB of the periodic table or of transition metals being less than 20 ppm.

10 Claims, No Drawings

AQUEOUS PHARMACEUTICAL FORMULATIONS OF SODIUM CROMOGLYCATE

This is a continuation of U.S. application Ser. No. 08/027,356, filed Mar. 8, 1993, now abandoned.

This invention relates to novel pharmaceutical formulations and methods for their preparation.

The disodium salt of 1,3-bis(2-carboxychromon-5-yloxy)-propan-2-ol, hereinafter called sodium cromoglycate, is known to be highly efficacious in the treatment of allergic conditions of the eye, nose, gastro-intestinal tract and lungs. United Kingdom Patent No 1399834 describes a method for preparation of a clear aqueous solutions of sodium cromoglycate which are useful for the treatment of such conditions.

International Patent Application No WO 90/13284 discloses solutions of sodium cromoglycate made viscous by the presence of a carbomer (a polymer of acrylic acid cross-linked with a polyalkenyl polyether) as viscosity modifying agent.

European Patent Application No EP-A-413583 discloses aqueous solutions of sodium cromoglycate containing inter alia more than 20 ppm of ions of metals of groups IIA, IB, IIB and IVB of the periodic table and of transition metals.

However, it is-desirable for formulations for treatment of allergic conditions, especially those of the eye, to contain the minimum number of excipients necessary.

Nevertheless, in formulations for the treatment of the eye, it is usual to combine an aqueous solution of sodium cromoglycate with a tonicity modifying agent to reduce the irritation on administration of the medicament. Sodium chloride is a widely used tonicity modifying agent, and its use in solutions of sodium cromoglycate has been taught in the above mentioned UK patent.

Whilst sodium chloride may be used as a tonicity modifying agent for aqueous solutions of sodium cromoglycate when the sodium cromoglycate concentration is relatively low, we have found that with higher concentrations of sodium cromoglycate, or on standing for long period of time, this excipient may cause undesirable precipitation of the sodium cromoglycate. In particular, sodium chloride causes a reduction in solubility of sodium cromoglycate in aqueous solution which is especially unacceptable for sodium cromoglycate concentrations of more than 2% w/v. Here and elsewhere the concentration of active ingredient is based on anhydrous weight of sodium cromoglycate.

We have discovered that non-ionic tonicity modifying agents are much more satisfactory at maintaining the solubility of sodium cromoglycate at high concentration in aqueous solution. Nevertheless, many of the non-ionic substances which are reported to be useful as tonicity modifying agents have been found to have other undesirable properties. The substances polyethylene glycol and polypropylene glycol have been reported to cause allergic reactions in the eye in some patients. Furthermore, polyethylene glycol can in some cases be incompatible with plastic materials used to manufacture the container for the medicament. Sugars, such as lactose, sucrose, mannitol and sorbitol, are good growth media for microorganisms, and as such are not, in the absence of a high concentration of antimicrobial preservative or sterilant, ideal excipients for use in pharmaceutical formulations for adminstration to the eye.

Surprisingly, we have found that glycerol may be used as an tonicity modifying agent for aqueous solutions of sodium cromoglycate, which substance possesses none of the above mentioned undesirable properties of sodium chloride, nor the undesirable properties of the above mentioned other non-ionic tonicity modifying agents.

According to the invention, therefore, we provide a pharmaceutical formulation comprising a substantially clear aqueous solution having a viscosity of less than 10 mPa.s containing 3.5 to 5% w/v of 1,3-bis(2-carboxychromon-5-yloxy)-propan- 2-ol, or a pharmaceutically acceptable salt thereof, as active ingredient and glycerol, the concentration of ions of metals of groups IIA, IB, IIB and IVB of the periodic table or of transition metals being less than 20 ppm.

We prefer that the formulation contains sodium cromoglycate as active ingredient.

The formulation will preferably contain 4% w/v of active ingredient.

The formulation will contain the glycerol as tonicity modifying agent at a concentration which will be appropriate for administration to the eye; for instance so that the solution is isotonic with lacrymal fluid.

Body fluids, including blood and lacrymal fluid, normally have an osmotic pressure which corresponds to that of 0.9% sodium chloride.

The 0.9% sodium chloride can be said to be iso-osmotic (isotonic) with physiological fluids. Solute concentration can be expressed in terms of osmoles or milliosmoles, although it is preferable to express the concentration terms osmolarity and osmolality in terms of moles of solute particles; osmolarity is the concentration expressed per liter of solution and osmolality is the concentration per kilogramme of water. The measured osmolality of 0.9% w/v aqueous sodium chloride and plasma is approximately 290 mmol per kilogramme.

For a formulation containing 4% sodium cromoglycate, we prefer that the glycerol is used at a concentration of 0.85 to 3.4% w/v, preferably 1.3 to 2.1% w/v, especially 1.7% w/v. Sodium cromoglycate has a tonicity of approximately 22 mosm per 1% concentration in solution. Therefore, for example, at lower concentrations of sodium cromoglycate, a somewhat larger amount of tonicity modifying agent will be appropriate.

The viscosity of the solution at ambient temperature will be less than 10 mPa.s, preferably less than 5 mPa.s. It is particularly preferred that the viscosity does not differ appreciably from that of water.

In addition the formulation may also contain an effective proportion of a pharmaceutically acceptable chelating or sequestering agent. Suitable chelating or sequestering agents include sodium carboxymethyl cellulose, citric, tartaric or phosphoric acid, and amino carboxylate compounds, preferably ethylenediamine tetra acetic acid or its salts especially its disodium salt. Further examples include glycine and derivatives, e.g. N,N-dihydroxy ethyl glycine and its salts, e.g. its sodium salt.

The concentration of the chelating or sequestering agent may vary considerably, but in any case should be such as to ensure that no precipitation of metal salts of the active ingredient occurs. A suitable concentration may be from 0.01% to 0.1%, although when the concentration of metal ions is very low (for example less than 0.4 ppm) the chelating or sequestering agent may be dispensed with, if desired. By the term "metal ions", we mean ions of metals in groups IIA, IB, IIB, IVB and the transition metals, in the periodic table. $Pb^{2+}$, $Ca^{2+}$, $Mg^{2+}$, $Fe^{2+}$, $Fe^{3+}$ and $Zn^{2+}$ ions are particularly detrimental in concentrations above 20 ppm.

The formulation may, if desired, contain an effective proportion of a pharmaceutically acceptable antimicrobial preservative or sterilising agent. Suitable antimicrobial preservatives include pharmaceutically acceptable quaternary ammonium salts. The preferred preservatives amongst the quaternary ammonium compounds are the alkyl benzyl dimethyl ammonium chlorides and mixtures thereof, e.g. that known generically as 'benzalkonium chloride'. The preservative may be used at a concentration of from about 0.005% to 0.1% w/v, preferably from 0.005% to 0.05% w/v, most preferably about 0.01% w/v. Another suitable preservative is chlorbutol. The concentration of chlorbutol in solution should be such that the bacterial growth in the formulation is inhibited. We have found that acceptable concentrations of chlorbutol are greater than 0.25% w/v but that the upper limit for the concentration of chlorbutol is about 0.6% w/v. Yet more suitable preservatives are described in UK Patent No 1399834.

The formulation may be prepared by standard means for the preparation of sterile solutions. For comfort in use it is preferred to adjust the pH of the solution to be in the range pH 4.5 to 7.5, preferably pH 5.5 to 7.5, more preferably pH 6.0 to 7.0, yet more preferably pH 6.2 to 6.8 especially pH 6.5.

The formulations of the invention are indicated for use in the treatment of vernal kerato conjunctivitis, the ocular symptoms of hay fever, marginal corneal infiltration and generally of allergic conditions of the eye. Typically, a dosage of 1 or 2 drops (i.e. from about 0.66 mg to 2.64 mg of active ingredient) into the affected eye up to 4 times a day is indicated. In ophthalmic and nasal use, the unpreserved compositions may be put in single application containers containing from 0.3 to 0.7 ml of solution (typically from 10 to 35 mg of active ingredient) and the preserved compositions may be put in multi-dose (plastic, e.g. polyethylene, or glass) packs containing 5 to 30 ml of solution.

The formulations according to the invention are advantageous in that they are more stable, more efficacious, have a longer effect, are less allergenic, produce fewer side effects, or have other advantageous properties when compared with other formulations of the active ingredient.

The invention is illustrated, but in no way limited, by the following example:

EXAMPLE 1

An Unpreserved Eye-Drop Solution

| | |
|---|---|
| Sodium cromoglycate BP | 4.00% w/v |
| Glycerol BP | 1.70% w/v |
| Disodium edetate BP | 0.01% w/v |
| Sodium hydroxide solution (Analar): as required to adjust to pH 6.5 | |
| Purified water | to 100% |

Method 1600 g of sodium cromoglycate and 4 g of sodium edetate were dissolved with stirring in 30 liters of purified water. 680 g of glycerol were added, and the pH adjusted to pH 6.5 with 0.1M aqueous sodium hydroxide solution. The solution was made up to 40 liters with more water, sterile filtered and filled into single use containers of minimum volume 0.35 ml.

We claim:

1. A pharmaceutical formulation comprising a substantially clear aqueous solution having a viscosity of less than 10 mPa.s containing 3.5 to 5% w/v of 1,3-bis(2-carboxychromon- 5-yloxy)-propan-2-ol, or a pharmaceutically acceptable salt thereof, as active ingredient and glycerol, the concentration of ions of metals of groups IIA, IB, IIB, and IVB of the periodic table or of transition metals being less than 20 ppm, wherein the formulation is free of a viscosity modifying agent.

2. A pharmaceutical formulation according to claim 1, wherein the active ingredient is sodium cromoglycate.

3. A pharmaceutical composition according to claim 1, wherein the concentration of glycerol is between 0.85 to 3.4% w/v.

4. A pharmaceutical formulation according to claim 3 wherein the concentration of glycerol is between 1.3 and 2.1% w/v.

5. A pharmaceutical formulation according to claim 1, wherein the pH is between 4.5 and 7.5.

6. A pharmaceutical formulation according to claim 5, wherein the pH is between 6.0 and 7.0.

7. A pharmaceutical formulation according to claim 1 comprising 4% w/v sodium cromoglycate, 1.7% w/v glycerol, 0.01% disodium edetate and sufficient sodium hydroxide to adjust the pH of the solution to pH 6.5.

8. A pharmaceutical formulation according to claim 1, further comprising an effective proportion of an antimicrobial preservative or sterilizing agent or both.

9. A pharmaceutical pack comprising a formulation according to claim 1 and containing from 10 to 35 mg of active ingredient in unit dosage form.

10. A method of treatment of conditions of the eye in which allergy plays a contributory part, which method comprises administering a therapeutically effective amount of a solution according to claim 1 to the eye of a patient suffering from such a condition.

* * * * *